(12) United States Patent
Peters

(10) Patent No.: US 10,229,192 B2
(45) Date of Patent: Mar. 12, 2019

(54) HIERARCHICAL DE-DUPLICATION TECHNIQUES FOR TRACKING FITNESS METRICS

(71) Applicant: Under Armour, Inc., Baltimore, MD (US)

(72) Inventor: Christopher Peters, Austin, TX (US)

(73) Assignee: Under Armour, Inc., Baltimore, MD (US)

( * ) Notice: Subject to any disclaimer, the term of this patent is extended or adjusted under 35 U.S.C. 154(b) by 415 days.

(21) Appl. No.: 14/798,588

(22) Filed: Jul. 14, 2015

(65) Prior Publication Data

US 2016/0188693 A1   Jun. 30, 2016

Related U.S. Application Data

(60) Provisional application No. 62/024,129, filed on Jul. 14, 2014.

(51) Int. Cl.
  *G06F 7/00*    (2006.01)
  *G06F 17/30*   (2006.01)
  *G06F 19/00*   (2018.01)
  *G06F 1/16*    (2006.01)

(52) U.S. Cl.
  CPC .... *G06F 17/30702* (2013.01); *G06F 19/3481* (2013.01); *G06F 1/163* (2013.01)

(58) Field of Classification Search
  CPC ...................................................... G06F 1/163
  USPC ........................................................ 707/748
  See application file for complete search history.

(56) References Cited

U.S. PATENT DOCUMENTS

| | | | | |
|---|---|---|---|---|
| 7,811,201 B1* | 10/2010 | Mikan | ................ | A63B 24/0062 482/4 |
| 8,795,138 B1* | 8/2014 | Yeh | ........................ | A61B 5/7415 482/8 |
| 8,903,671 B2* | 12/2014 | Park | ........................ | G08B 21/18 702/104 |
| 9,795,855 B2* | 10/2017 | Jafarifesharaki | ....... | H04L 67/42 |
| 2013/0138230 A1* | 5/2013 | Landers | .................. | G06F 17/40 700/91 |
| 2013/0228063 A1* | 9/2013 | Turner | ..................... | G10H 1/40 84/612 |
| 2014/0164611 A1* | 6/2014 | Molettiere | ............ | A61B 5/1112 709/224 |
| 2014/0245161 A1* | 8/2014 | Yuen | ....................... | H04W 4/21 715/736 |

* cited by examiner

*Primary Examiner* — Eliyah S. Harper
(74) *Attorney, Agent, or Firm* — Maginot, Moore & Beck LLP

(57) ABSTRACT

A method is provided for tracking fitness data. A server device receives a first instance of fitness data from a first device and a second instance of fitness data from a second device. The fitness data comprises information about exercise activity of a user. The server determines that the first instance of the fitness data was received from the first device and that the second instance of the fitness data was received from the second device. The server selects a preferred instance of the fitness data comprising one of the first instance of the fitness data or the second instance of the fitness data based on a classification of the first instance and the second instance. The server incorporates the preferred instance of the fitness data into a fitness profile of the user.

9 Claims, 4 Drawing Sheets

HIERARCHICAL DE-DUPLICATION TECHNIQUES FOR TRACKING FITNESS METRICS

RELATED APPLICATIONS

This application claims priority from U.S. Provisional Patent Application No. 62/024,129 filed on Jul. 14, 2014, the entirety of which is incorporated by reference herein.

TECHNICAL FIELD

The present disclosure relates to techniques for tracking fitness metrics.

BACKGROUND OF THE INVENTION

Electronic devices are commonly used to track biometric data of an individual over the course of a day. For example, fitness devices may be used to track an individual's fitness activity (e.g., step count, heart rate, pulse count, exercise intensity, etc.) and sleep activity. Fitness devices are ubiquitous, and individuals may wear multiple fitness devices to track multiple types of activities. For example, an individual may wear a heart rate monitor during dedicated exercises and may wear a pedometer during the entire course of the day.

DETAILED DESCRIPTION OF EXAMPLE EMBODIMENTS

Overview

A method is provided for tracking fitness data. A server device receives a first instance of fitness data from a first device and a second instance of fitness data from a second device. The fitness data comprises information about exercise activity of a user. The server determines that the first instance of the fitness data was received from the first device and that the second instance of the fitness data was received from the second device. The server selects a preferred instance of the fitness data comprising one of the first instance of the fitness data or the second instance of the fitness data based on a classification of the first instance and the second instance. The server incorporates the preferred instance of the fitness data into a fitness profile of the user.

Example Embodiments

The techniques presented herein relate to tracking fitness activity data. Specifically, the techniques described herein enable a server to receive fitness data from one or more monitoring devices, and to select one or more instances of the fitness data to be incorporated into a fitness profile of a user.

Figure 1:
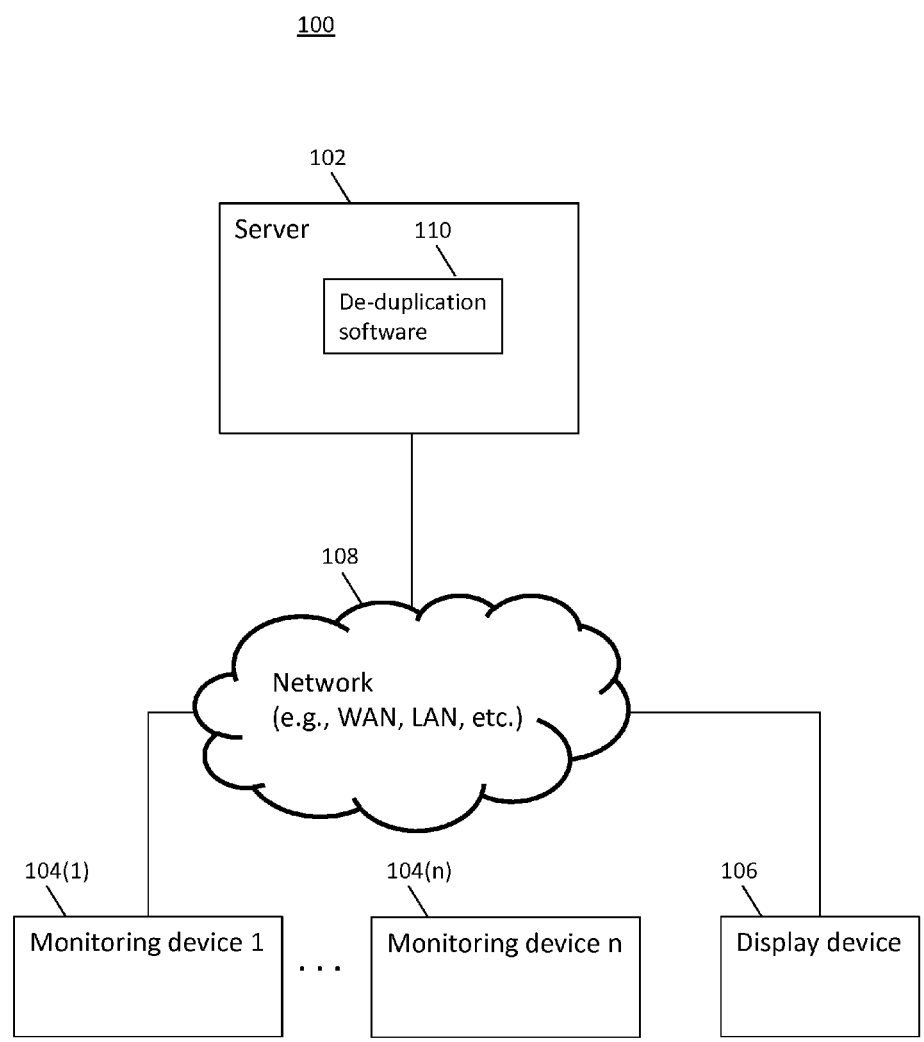
FIG. 1 shows an example system topology depicting a server configured to perform de-duplication operations based on fitness data received from one or more monitoring devices.

FIG. 1 shows an example system topology 100 ("system") that has a server 102, a plurality of monitoring devices 104(1)-104(n) and a display device 106. The server 102, monitoring devices 104(1)-104(n) and display device 106 are configured to communicate with each other over a network 108. The network may be for example, a Wide Area Network (WAN) (e.g., the Internet), a Local Area Network (LAN), a Personal Area Network (PAN), etc. In one example, the server 102, monitoring devices 104(1)-104(n) and the display device 106 are configured to send and receive communications (e.g., data packets) to each other via the network 108. As described by the techniques herein, these communications may contain fitness data information that describes information about an exercise activity of a user. For example, a user (not shown in FIG. 1) may wear one or more of the monitoring devices 104(1)-104(n) or may have one or more of the monitoring devices 104(1)-104(n) affixed to the user's person. Over the course of a day or portions of a day, the monitoring devices 104(1)-104(n) may collect exercise data and sleep data and may send information of the exercise data to a server. Likewise, in one example, the server 102 is configured to send to the monitoring devices 104(1)-104(n) and/or the display device 106 communications (messages) with presentation instructions.

In general, the server 102 is a network device (e.g., a computing device and/or a mobile device) that is configured to send and receive communications in the system (e.g., via the network 108). The server 102 may process packets received by other devices in the system and may store executable software (e.g., computer/processor executable logic) to classify data received by the other devices in the system. For example, as described herein, the server 102 may store de-duplication software 110 to select appropriate fitness data received by the one or more monitoring devices 104(1)-104(n) to be processed for a user's overall fitness profile and to send to the monitoring devices 104(1)-104(n) and/or the display device 106 presentation instruction messages to display to the user fitness profile information comprising fitness data for the individual. The fitness profile of the user may contain fitness information of the user displaying, for example, biometric information of a user during a workout or over the course of a day. The fitness profile may contain information accessible by the user or other entities that display health information of the user and exercise information of the user (e.g., step count, heart rate, distance traveled, workout time, workout frequency, workout intensity, sleep information, nutrition information, location information, etc.).

FIG. 1 shows a plurality of monitoring devices 104(1)-104(n). The monitoring devices 104(1)-104(n) are devices configured to record fitness data information (e.g., exercise activity of a user). For example one monitoring device may be a pedometer configured to count a user's steps over the course of a day. Another monitoring device may be a heart rate monitor configured to measure heart rate biometrics for a user during a workout session. In another example, a monitoring device may be a sleep tracking device that tracks a user's sleep quality and quantity. It should be appreciated that these devices are merely examples, and that any one of the monitoring devices 104(1)-104(n) may be a health wearable device known or heretofore contemplated or any other device known to sense, measure and/or report activities related to a user's physiology, fitness, exercise, sleep, nutrition, diet, etc.

In one example, multiple ones of the monitoring devices 104(1)-104(n) may report to the server the same fitness data at the same time. For example, monitoring device 104(1)

and monitoring device 104(n) may each be devices that record a step count for the user, and each of the monitoring devices may report the step count information to the server 104. Thus, the server 104 may receive duplicate fitness data over the course of a day. In order to provide an accurate fitness profile to the individual, the server may need to remove duplicate fitness data from an individual's overall fitness profile. For example, if monitoring device 104(1) and monitoring device 104(n) each send step count data of a user to the server 104 for the same physical activity, the server 106 will need to remove the step count data received by one of the monitoring devices in order to provide the accurate fitness profile. This process is referred to as "de-duplication."

Figure 2A:
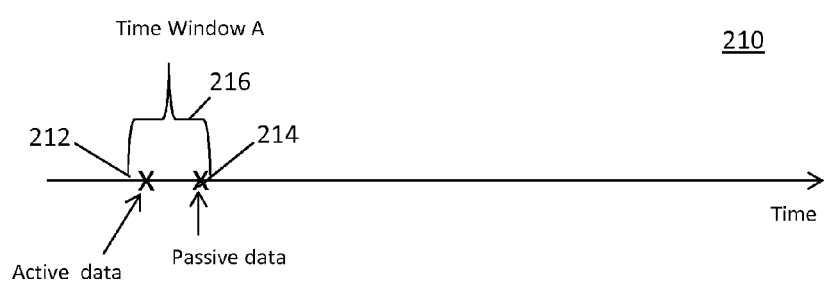
FIGS. 2A-2C show example diagrams representing fitness data received from one or more devices with different classifications.
Figure 2B:
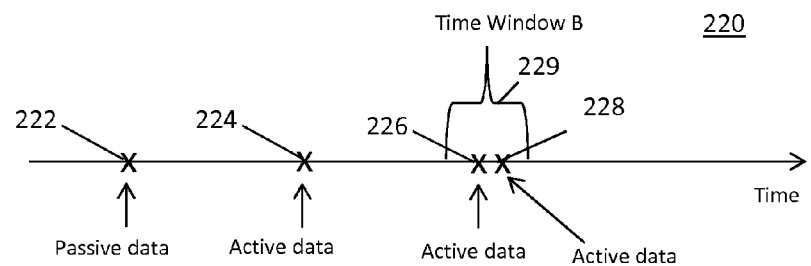
Figure 2C:
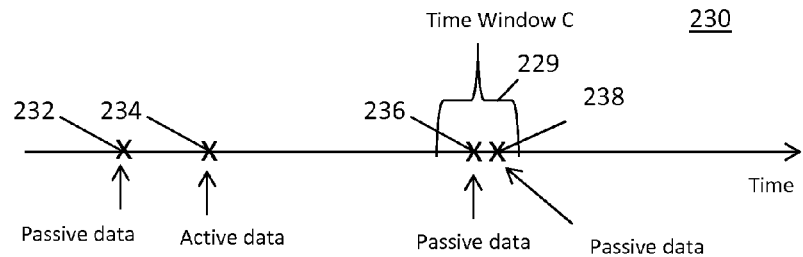

FIGS. 2A-2C show the server 106 receiving fitness data from one or more of the monitoring devices 104(1)-104(n) over a period of time. For example, timeline 210 in FIG. 2A shows the server 104 receiving instances of fitness data. The instances are shown at reference numeral 212 and 214. For example, the first instance 212 of fitness data may be received by a first monitoring device (e.g., monitoring device 104(1)), and the second instance 214 of fitness data may be received by a second monitoring device (e.g., monitoring device 104(n)). The first instance 212 and the second instance 214 in FIG. 2A are received over a time window 216, shown as time window A in FIG. 2A. The time window is a duration of time defined by the server 106 during which fitness data received by the server 106 is classified as being received simultaneously or substantially simultaneously. For example, time window A may be a predetermined period of time (e.g., five seconds), and any instances of fitness data received during time window A may be characterized as being received at the same time as each other. In other words, during a particular time window, the server 106 may receive multiple instances of fitness data, and the server 106 may classify these instances of data as being received simultaneously or substantially simultaneously.

The instances of fitness data may be classified into categories. For example, in FIG. 2A the first instance 212 of fitness data may be "active fitness data" ("active data") and the second instance 214 of fitness data may be "passive fitness data" ("passive data"). The passive fitness data represents activities that occur over the course of an individual's day (e.g., steps taken, stairs climbed, etc.), while active fitness data represents deliberate exercise activity undergone by the individual (e.g., running, working out, intentional physical activity). Monitoring devices 104(1)-104(n) may be configured to monitor passive data only, active data only or both active and passive data.

As stated above, in FIG. 2A, the server 104 receives the first instance 212 of fitness data, which is active data, and the second instance 214, which is passive data at substantially the same time (e.g., substantially simultaneously during time window A). The server 104, upon receiving the first instance 212 may determine that the first instance 212 of fitness data is active data. Likewise, upon receiving the second instance 214, the server 104 may determine that the second instance 214 is passive data. In one example, the server 104 may determine the active/passive classifications on its own based on information contained within the message containing the first instance 212 and/or the second instance 214. The server 104 may then prioritize certain classifications over others. For example, when data is received substantially simultaneously, the server 104 may prioritize the active data over the passive data. In this example, the server 104 will select the active data (e.g., the first instance 212) to be included in a user's fitness profile and will discard or de-duplicate the non-selected instance (e.g., the passive data of the second instance 214). In another example, when the data is received substantially simultaneously, the server 104 may prioritize the passive data and may de-duplicate the active data. In a preferred, non-limiting embodiment, the server 104 prioritizes active data over passive data.

Reference is now made to FIG. 2B. FIG. 2B shows a timeline 220 with a series of instances 222, 224, 226, and 226 of fitness data received by the server 104. In FIG. 2B, passive data 222 is included in the user's fitness profile. It is not de-duplicated or discarded since there was no other instance received substantially simultaneously. In other words, in one example, the server 104 will not de-duplicate or discard instances of fitness data when the instance is the only instance of fitness data received at a particular time. Thus, in FIG. 2B, passive data 222 and active data 224 are not de-duplicated since there is no other instance received substantially simultaneously as these instances.

However, in FIG. 2B, instance 226 and instance 228 are received substantially simultaneously (as defined by time window B 229). Thus, the server 104 will need to de-duplicate instance 226 and instance 228. Since instance 226 and instance 228 are both instances of active data, the server 104 cannot de-duplicate based on this classification alone. The server 104, may, however, have other mechanisms by which data is de-duplicated. For example, the server 104 may select as the preferred instance of fitness data the instance that is received first. In FIG. 2B, instance 226 is received before instance 228, and thus, the server 104 may select instance 226 as the preferred instance and may discard or de-duplicate instance 228 since it received after instance 226. In other words, the server 104 may de-duplicate data on a first-in, first-out (FIFO) basis, selecting the instance of data that is received first in a given time window. In another example, the server 104 may de-duplicate data on a last-in, first-out (LIFO) basis, selecting the instance of data that is received last in a given time window. Thus, in general, the server 104 may de-duplicate instances of data from a user's fitness profile based on when an instance of data is received relative to other instances of data.

FIG. 2C shows a timeline 230 that is similar to FIG. 2B, with the exception that in the time window (time window C) in FIG. 2C, instances 236 and 238 of passive data are shown. That is, FIG. 2C shows instances 232, 234, 236 and 238 are shown. Instance 234 is an instance of passive data, while instance 236 is an instance of active data. Both instance 234 and instance 236 are included in a user's fitness profile (e.g., these instances are not de-duplicated since there is no other instance received at substantially the same time as these instances). Since instance 236 and 238 are received substantially simultaneously, the server 104 may de-duplicate one of these instances. Instance 236 and instance 238 are both instances of passive data, and the server 104 cannot de-duplicate based on this classification alone. Instead, in this example, the server 104 may have a priority ranking or hierarchical ranking of devices, and may de-duplicate instances of data based on the position of the device sending the instance of data in the priority ranking/hierarchical ranking. For example, instance 236 may be sent to the server 104 by monitoring device 104(1) and instance 238 may be sent to the server 104 by monitoring device 104(n). As shown in Table 1, below, the server 104 may maintain a priority ranking and/or hierarchical ranking of monitoring devices, and in one example, monitoring device 104(1) may have a higher priority ranking/hierarchical ranking than monitoring device 104(n). In this example, instance 236 will be included in the user's fitness profile and instance 238 will be de-duplicated from the user's fitness data.

TABLE 1

Priority/Hierarchical ranking of monitoring devices

| Monitoring Device | Priority |
|---|---|
| 104(1) | Rank 1 |
| 104(2) | Rank 2 |
| 104(n) | Rank 3 |

It should be appreciated that this is merely an example, and that the server 104 may retain any combination/permutation of hierarchy and/or priority of the monitoring devices. Furthermore, it should be appreciated that the server 104 may generate the ranking on an ad hoc basis, as monitoring devices communicate with the server 104. In another example, the server 104 may maintain the ranking on an a priori basis (e.g., by generating the ranking before instances of data are sent to the server 104 and/or by receiving from another device/entity a ranking/hierarchy of monitoring devices). Thus, the server 104 may select to be included in a user's fitness profile preferred instances of data received from monitoring devices that have high relative priority rankings when compared to priority rankings of other monitoring devices. In one example, instances of data from certain types of monitoring devices (e.g., heart rate monitors) may have higher priorities than instances of other types of monitoring devices (e.g., step counters).

Figure 3:
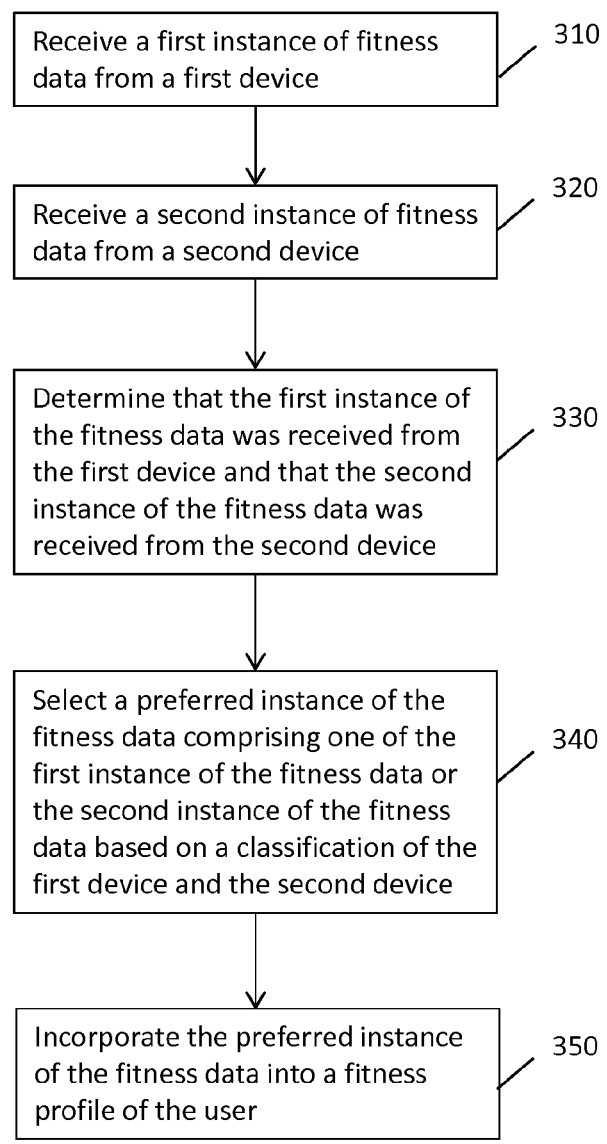
FIG. 3 shows an example flow chart depicting operations of the server performing de-duplication operations.

Reference is now made to FIG. 3 shows an example flow chart 300 depicting de-duplication operations performed by the server 104. At operation 310, the server 104 receives a first instance of fitness data from a first device (e.g., a first monitoring device). The fitness data comprises information about exercise activity of a user. At operation 320, the server 104 receives a second instance of the fitness data from a second device. The server 104, at operation 330, determines that the first instance of the fitness data was received from the first device and that the second instance of the fitness data was received from the second device. At operation 340, the server 104 selects a preferred instance of the fitness data comprising one of the fitness instance of the fitness data or the second instance of the fitness data based on a classification of the first instance and the second instance. The server 104, at operation 350, incorporates the preferred instance of the fitness data into a fitness profile of the user. The server receives fitness data from one or more monitoring devices. The server determines a priority for the monitoring devices and selects fitness data received by a device with the highest priority. Thus, the server is able to de-duplicate similar or identical fitness data received at the same time instance.

Figure 4:
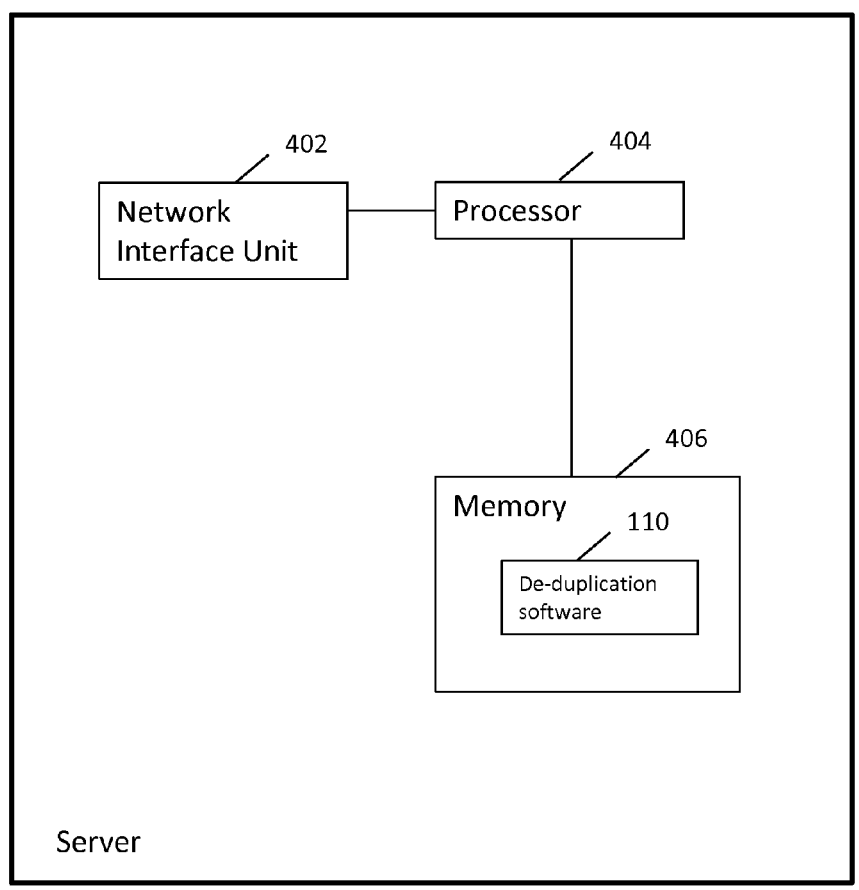
FIG. 4 shows an example block diagram depicting the server configured to perform the de-duplication operations, according to an example embodiment.

Reference is now FIG. 4, which shows an example block diagram of the server 104. The server 104 is configured, for example, to de-duplicate an instance or instances of fitness data. The server 104 has a network interface unit 402, a processor 404 and a memory 406. The network interface unit 402 is configured to send and receive communications to and from devices in the system 100 (e.g., the monitoring devices 104(1)-104(n) and the display device 106). For example, the network interface unit 402 receives instances of fitness data over time (e.g., over the course of a day) from one or more of the monitoring devices 104(1)-104(n). The network interface unit 402 is coupled to the processor 404. The processor is, for example, a microprocessor or microcontroller that is configured to execute program logic instructions (i.e., software) for carrying out various operations and tasks of the server 104, as described above. For example, the processor 404 is configured to execute de-duplication software 110 according to the techniques described above. The functions of the processor 404 may be implemented by logic encoded in one or more tangible computer readable storage media or devices (e.g., storage devices, compact discs, digital video discs, flash memory drives, etc. and embedded logic such as an application specific integrated circuit, digital signal processor instructions, software that is executed by a processor, etc.).

The memory 406 may comprise read only memory (ROM), random access memory (RAM), magnetic disk storage media devices, optical storage media devices, flash memory devices, electrical, optical, or other physical/tangible (non-transitory) memory storage devices. The memory 406 stores software instructions for the de-duplication software 110.

The de-duplication software 110 may take any of a variety of forms, so as to be encoded in one or more tangible computer readable memory media or storage device for execution, such as fixed logic or programmable logic (e.g., software/computer instructions executed by a processor), and the processor 404 may be an application specific integrated circuit (ASIC) that comprises fixed digital logic or a combination thereof.

For example, the processor 404 may be embodied by digital logic gates in a fixed or programmable digital logic integrated circuit, which digital logic gates are configured to perform the de-duplication software 110. In general, the de-duplication software 110 may be embodied in one or more computer readable storage media encoded with software comprising computer executable instructions and when the software is executed operable to perform the operations described herein.

In summary, a method is provided comprising: at a server, receiving a first instance of fitness data from a first device, wherein the fitness data comprises information about exercise activity of a user; receiving a second instance of the fitness data from a second device; determining that the first instance of the fitness data was received from the first device and that the second instance of the fitness data was received from the second device; selecting a preferred instance of the fitness data comprising one of the first instance of the fitness data or the second instance of the fitness data based on a classification of the first instance and the second instance; and incorporating the preferred instance of the fitness data into a fitness profile of the user.

In addition, one or more computer readable storage media is provided that is encoded with software comprising computer executable instructions and when the software is executed operable to: receive a first instance of fitness data from a first device, wherein the fitness data comprises information about exercise activity of a user; receive a second instance of the fitness data from a second device; determine that the first instance of the fitness data was received from the first device and that the second instance of the fitness data was received from the second device; select a preferred instance of the fitness data comprising one of the first instance of the fitness data or the second instance of the fitness data based on a classification of the first device and the second device; and incorporate the preferred instance of the fitness data into a fitness profile of the user.

Furthermore, an apparatus is provided comprising: a network interface unit; and a processor unit coupled to the network interface unit and configured to: receive via the network interface unit a first instance of fitness data from a first device, wherein the fitness data comprises information about exercise activity of a user; receive via the network interface unit a second instance of the fitness data from a second device; determine that the first instance of the fitness data was received from the first device and that the second instance of the fitness data was received from the second device; select a preferred instance of the fitness data comprising one of the first instance of the fitness data or the second instance of the fitness data based on a classification of the first device and the second device; and incorporate the preferred instance of the fitness data into a fitness profile of the user.

It should be appreciated that the techniques described above in connection with all of the embodiments may be performed by one or more computer readable storage media that is encoded with software comprising computer executable instructions to perform the methods, operations and steps described herein. For example, the de-duplication operations performed by the server 104 may be performed by one or more computer or machine readable storage media (non-transitory) or device executed by a processor and comprising software, hardware or a combination of software and hardware to perform the techniques described herein. Thus, it is intended that the present embodiments covers the modifications and variations of this invention provided they come within the scope of the claims and their equivalents.

What is claimed is:

1. A method for tracking fitness data, the method comprising:
    attaching a first monitoring device and a second monitoring device to a user, the first monitoring device and the second monitoring device configured to collect a same type of fitness data from the user;
    at a server, defining a time window during a workout session of the user and receiving a first instance of fitness data within the defined time window from the first monitoring device carried by the user during the workout session, wherein the fitness data comprises information about exercise activity of the user during the workout session, and wherein the first monitoring device has a first priority ranking;
    receiving a second instance of the fitness data within the defined time window from the second monitoring device carried by the user during the workout session, wherein the second monitoring device has a second priority ranking;
    receiving a third instance of the fitness data from the first monitoring device during the workout session but outside of the defined time window;
    receiving a fourth instance of the fitness data from the second monitoring device during the workout session but outside of the defined time window;
    determining that the first instance of the fitness data and the third instance of the fitness data were received from the first monitoring device and that the second instance of the fitness data and the fourth instance of the fitness data were received from the second monitoring device;
    determining a classification of each of the first instance, second instance, third instance and fourth instance of the fitness data as either an instance of active exercise activity or an instance of passive exercise activity;
    obtaining a set of rules that define a preferred instance of fitness data received within the defined time window as a function of (i) the classification of each instance of fitness data as active or passive fitness data, (ii) a time received for each instance of fitness data within the defined time window; and (iii) the priority ranking of each instance of fitness data based on the health wearable device the instance of fitness data originated from;
    selecting a preferred instance of the fitness data comprising one of the first instance of the fitness data and the second instance of the fitness data based on the set of rules, wherein selecting the preferred instance of the fitness data comprises:
        selecting the first instance as the preferred instance of the fitness data when the first instance is an instance of active exercise activity and when the second instance is an instance of passive exercise activity;
        selecting the first instance as the preferred instance of the fitness data when both the first instance and the second instance are an instance of active exercise activity and the first instance is received at a time before the second instance within the defined time window; and
        selecting the first instance as the preferred instance of the fitness data when both the first instance and the second instance are an instance of passive exercise activity and the first priority ranking of the first monitoring device is greater than the second priority ranking of the second monitoring device;
    incorporating the preferred instance of the fitness data, the third instance of the fitness data, and the fourth instance of the fitness data into a fitness profile of the user;
    discarding the non-selected instance of the fitness data such that it is not incorporated into the fitness profile of the user; and
    displaying a portion of the fitness profile of the user on a display device, the portion of the fitness profile including the selected preferred instance of the fitness data and not including the discarded non-selected instance of the fitness data.

2. The method of claim 1, wherein the determining a classification of each of the first instance and the second instance is indicative of a priority ranking of the first monitoring device and the second monitoring device relative to one another.

3. One or more non-transitory computer readable storage media encoded with software comprising computer executable instructions and when the software is executed operable to:
    define a time window;
    receive a first instance of fitness data from a first monitoring device within the defined time window, wherein the fitness data comprises information about exercise activity of a user;
    receive a second instance of the fitness data from a second monitoring device within the defined time window;
    determine a classification of each of the first monitoring device and the second monitoring device as either an active device or a passive device, and when said monitoring device is a passive device, determine a priority ranking for such passive device;
    receive a third instance of fitness data from the first monitoring device outside of the defined time window;
    receive a fourth instance of the fitness data from the second monitoring device within the defined time window;
    determine that the first instance of the fitness data and the third instance of the fitness data were received from the first monitoring device and that the second instance of the fitness data and the fourth instance of the fitness data were received from the second monitoring device;
    select a preferred instance of the fitness data comprising one of the first instance of the fitness data or the second instance of the fitness data based on the classification of the first monitoring device and the second monitoring device, wherein the instructions operable to select the preferred instance of the fitness data comprise instructions operable to:

select the first instance of the fitness data as the preferred instance of the fitness data when the first monitoring device is an active device and when the second monitoring device is a passive monitoring device;

select the first instance as the preferred instance of the fitness data when both the first monitoring device and the second monitoring device are active devices and the first instance was received at a time before the second instance within the defined time window; and select the first instance as the preferred instance of the fitness data when both the first monitoring device and the second monitoring device are passive monitoring devices and the priority ranking of the first monitoring device is greater than the priority ranking of the second monitoring device;

incorporate the preferred instance of the fitness data, the third instance of the fitness data, and the fourth instance of the fitness data into a fitness profile of the user;

discard the non-selected instance of the fitness data from being incorporated into the fitness profile of the user; and display a portion of the fitness profile of the user on a display device, the portion of the fitness profile including the selected preferred instance of the fitness data and not including the discarded non-selected instance of the fitness data.

4. An apparatus comprising:

a network interface unit; and a processor unit coupled to the network interface unit and configured to:

receive via the network interface unit a first instance and a third instance of fitness data from a first health wearable device, wherein the fitness data comprises information about exercise activity of a user;

receive via the network interface unit a second instance and a fourth instance of the fitness data from a second health wearable device;

determine that the first instance and the third instance of the fitness data was received from the first health wearable device and that the second instance and the fourth instance of the fitness data was received from the second health wearable device;

determine that the first instance of the fitness data and the second instance of fitness data were received within a defined time window;

determine that the third instance of the fitness data and the fourth instance of the fitness data were received outside of the defined time window;

obtain a set of rules that define a preferred instance of fitness data received within the defined time window as a function of (i) a classification of each instance of fitness data as active or passive fitness data, (ii) a time received for each instance of fitness data within the defined time window; and (iii) a priority ranking of each instance of fitness data based on the health wearable device the instance of fitness data originated from;

select a preferred instance of the fitness data comprising one of the first instance of the fitness data or the second instance of the fitness data based on the set of rules;

incorporate the preferred instance of the fitness data, the third instance of fitness data and the fourth instance of fitness data into a fitness profile of the user;

discard the non-selected instance of the fitness data from being incorporated into the fitness profile of the user; and display a portion of the fitness profile of the user on a display device, the portion of the fitness profile including the selected preferred instance of the fitness data and not including the discarded non-selected instance of the fitness data.

5. The method of claim 1 wherein the defined time window is a duration of time defined by the server during which fitness data received by the server is classified as being received simultaneously or substantially simultaneously.

6. The method of claim 5 further comprising displaying a portion of the fitness profile of the user on a display device, the portion of the fitness profile including the selected preferred instance of the fitness data and not including the discarded non-selected instance of the fitness data.

7. The method of claim 6 wherein the fitness data includes one or more of step count, heart rate, distance traveled, workout time, workout frequency, and workout intensity.

8. The method of claim 1 wherein the same type of fitness data is heart rate data.

9. The method of claim 1 wherein the same type of fitness data is step count data.

* * * * *